(12) United States Patent
Hohn et al.

(10) Patent No.: US 6,498,011 B2
(45) Date of Patent: Dec. 24, 2002

(54) METHOD FOR TRANSFORMATION OF ANIMAL CELLS

(75) Inventors: Barbara Hohn, Arlesheim (CH); Luca Rossi, Neuchatel (CH); Alicja Ziemienowicz, Gdansk (PL); Biserka Relic, Liege (BE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/768,412

(22) Filed: Jan. 24, 2001

(65) Prior Publication Data

US 2001/0044150 A1 Nov. 22, 2001

Related U.S. Application Data

(63) Continuation of application No. PCT/EP99/05256, filed on Jul. 22, 1999.

(30) Foreign Application Priority Data

Jul. 24, 1999 (GB) .............................................. 9816138

(51) Int. Cl.⁷ .......................... C12Q 1/68; C12N 15/63; C12N 15/85

(52) U.S. Cl. ....................... 435/6; 435/91.4; 435/320.1; 435/325

(58) Field of Search ........................... 536/23.1; 514/44; 435/320.1, 183, 325, 91.4, 6; 530/350

(56) References Cited

U.S. PATENT DOCUMENTS

| | | |
|---|---|---|
| 5,831,020 A | 11/1998 | Citovsky |
| 5,976,880 A | 11/1999 | Sautter et al. |

FOREIGN PATENT DOCUMENTS

| | | |
|---|---|---|
| EP | 0 434 616 | 6/1991 |
| WO | WO 95/05471 | 2/1995 |
| WO | WO 95/34647 | 12/1995 |
| WO | WO 97/12046 | 4/1997 |

OTHER PUBLICATIONS

Franz Durrenberger et al., Covalently bound VirD2 protein of Agrobacterium tumefaciens protects the T–DNA from exonucleolytic degradation, Proc. Natl. Acad. Sci. USA, pp. 9154–9158.*

Adam et al., "Nuclear Protein Import in Permeabilized Mammalian Cells Requires Soluble Cytoplasmic Factors", J. Cell Biol., vol. 111, pp. 807–816 (Sep. 1990).

Bevan et al., "A Chimaeric Antibiotic Resistance Gene as a Selectable Marker for Plant Cell Transformation", Nature, vol. 304, pp. 184–187 (Jul. 1983).

Blochlinger et al., "Hygromycin B Phosphotransferase as a Selectable Marker for DNA Transfer Experiments with Higher Eucaryotic Cells", Molecular and Cellular Biology, vol. 4, No. 12, pp. 2929–2931 (Dec. 1984).

Christie et al., "The *Agrobacterium tumefaciens* virE2 Gene Product is a Single–Stranded–DNA–Binding Protein that Associates with T–DNA", J. Bacteriol., vol. 170, No. 6, pp. 2659–2667 (Jun. 1988).

Chu et al., "Electroporation for the Efficient Transfection of Mammalian Cells with DNA", Nucl. Acids Res., vol. 15, No. 3, pp. 1311–1326 (1987).

Citovsky et al., "Nuclear Import of Agrobacterium VirD2 and VirE2 Proteins in Maize and Tobacco", Proc. Natl. Acad. Sci. USA, vol. 91, pp. 3210–3214 (Apr. 1994).

Citovsky et al., "Nuclear Localization of Agrobacterium VirE2 Protein in Plant Cells", Science, vol. 256, pp. 1802–1805 (Jun. 1992).

Crameri et al., "Improved Green Fluorescent Protein by Molecular Evolution Using DNA Shuffling", Nature Biotechnology, vol. 14, pp. 315–319 (Mar. 1996).

Filichkin et al., "Formation of a Putative Relaxation Intermediate During T–DNA Processing Directed by the *Agrobacterium tumefaciens* VirD1,D2 endonuclease", Molecular Microbiology, vol. 8, No. 5, pp. 915–926 (1993).

Guralnick et al., "Transport of DNA into the Nuclei of Xenopus Oocytes by a Modified VirE2 Protein of Agrobacterium", Plant Cell, vol. 8, pp. 363–373 (Mar. 1996).

Hansen et al., "T–Strand Integration in Maize Protoplasts After Codelivery of a T–DNA Substrate and Virulence Genes", Proc. Natl. Acad. Sci. USA, vol. 94, pp. 11726–11730 (Oct. 1997).

Herrera–Estrella et al., "A Bacterial Peptide Acting as a Plant Nuclear Targeting Signal: The Amino–Terminal Portion of Agrobacterium Vir–D2 Protein Directs a (–Galactosidase Fusion Protein into Tobacco Nuclei", Proc. Natl. Acad. Sci. USA, vol. 87, pp. 953.

Hodgson et al., "Virosomes: Cationic Liposomes Enhance Retroviral Transduction", Nature Biotech., vol. 14, pp. 339–342 (Mar. 1996).

Howard et al., "Activation of the T–DNA Transfer Process in Agrobacterium Results in the Generation of a T–Strand–Protein Complex: Tight Association of VirD2 with the 5' Ends of T–Strands", Proc. Natl. Acad. Sci. USA, vol. 86, No. 11, pp. 4017–4021 (Jun.

Jordan et al., "Transfecting Mammalian Cells: Optimization of Critical Parameters Affecting Calcium–Phosphate Precipitate Formation", Nuc. Acids Res., vol. 24, No. 4, 596–601 (1996).

(List continued on next page.)

*Primary Examiner*—Andrew Wang
(74) *Attorney, Agent, or Firm*—Susan Hess

(57) ABSTRACT

The present invention relates to a method for introducing nucleic acids into cells for e.g. producing transiently transfected or stably transformed animal cells by using a specifically designed nucleic acid/protein complex comprising in operable linkage to an expressible DNA or to an oligonucleotide a VirD2 protein, preferably together with a VirE2 protein.

6 Claims, No Drawings

OTHER PUBLICATIONS

Knauf et al., "Wide Host Range Cloning Vectors: A Cosmid Clone Bank of an Agrobacterium Ti Plasmid", Plasmid, vol. 8, pp. 45–54 (1982).

Ludin et al., "Application of Novel Vectors for GFP–Tagging of Proteins to Study Microtubule–Associated Proteins", Gene, vol. 173, pp. 107–111 (1996).

Mullis et al., "[21] Specific Synthesis of DNA in Vitro via a Polymerase–Catalyzed Chain Reaction", Meth. Enzymol., vol. 155, pp. 335–350 (1987).

Neuhaus et al., "Transgenic Rapeseed Plants Obtained by the Microinjection of DNA into Microspore–Derived Embryoids", Theor. Appl. Genet., vol. 75, pp. 30–36 (1987).

O'Brien et al., "Construction and Characterization of a One–Plasmid System for the Controlled Expression of Genes in Mammalian Cells by Tetracycline", Gene, vol. 184, pp. 115–120 (1997).

Pansegrau et al., "Site–Specific Cleavage and Joining of Single–Stranded DNA by VirD2 Protein of *Agrobacterium tumefaciens* Ti Plasmids: Analogy to Bacterial Conjugation", Proc. Natl. Acad. Sci. USA, vol. 90, pp. 11538–11542 (Dec. 1993).

Potrykus et al., "Direct Gene Transfer: State of the Art and Future Potential", Plant Mol. Biol. Rep., vol. 3, No. 3, pp. 117–128 (1985).

Robertson et al., "Evolution of the Herpes Thymidine Kinase: Identification and Comparison of the Equine Herpesvirus 1 Thymidine Kinase Gene Reveals Similarity to a Cell–Encoded Thymidylate Kinase", Nucl. Acids Res., vol. 16, No. 23, pp. 11303–11317 (1988.

Rossi et al., "The VirD2 Protein of *Agrobacterium tumefaciens* Carries Nuclear Localization Signals Important for Transfer of T–DNA to Plants", Mol. Gen. Genet., vol. 239, pp. 345–353 (1993).

Schocher et al., "Co–Transformation of Unlinked Foreign Genes into Plants by Direct Gene Transfer", Bio/Technology, vol. 4, pp. 1093–1096 (1986).

Shillito et al., "High Efficiency Direct Gene Transfer to Plants", Bio/Technology, vol. 3, pp. 1099–1103 (Dec. 1985).

Southern, "Detection of Specific Sequences Among DNA Fragments Separated by Gel Electrophoresis", J. Mol. Biol., vol. 98, pp. 503–517 (1975).

Tinland et al., "The *Agrobacterium tumefaciens* Virulence D2 Protein is Responsible for Precise Integration of T–DNA into the Plant Genome", EMBO J., vol. 14, No. 14, pp. 3585–3595 (1995).

Tinland et al., "The T–DNA–Linked VirD2 Protein Contains Two Disntinct Functional Nuclear Localization Signals", Proc. Natl. Acad. Sci. USA, vol. 89, pp. 7442–7446 (Aug. 1992).

Wang et al., "Transient Expression of Foreign Genes in Rice, Wheat and Soybean Cells Following Particle Bombardment", Plant Mol. Biol., vol. 11, pp. 433–439 (1988).

* cited by examiner

METHOD FOR TRANSFORMATION OF ANIMAL CELLS

This application is a continuation of International Application PCT/EP99/05256, filed Jul. 22, 1999.

FIELD OF THE INVENTION

The present invention generally relates to the transformation of eukaryotic cells, particularly animal cells, with exogenous nucleic acids and to the generation of transgenic organisms generated from such cells. More particular, the present invention relates to a method for introducing nucleic acids into cells for producing transiently transfected/transformed or stably transformed cells by using a specifically designed nucleic acid/protein complex, as well as to cells transfected or transformed thereby.

BACKGROUND OF THE INVENTION

Several methods have been developed for introducing exogenous DNA molecules into eukaryotic cells in order to take advantage of the widespread benefits arising from the application of recombinant DNA technology to the production of transiently transfected/transformed cells as well as to transgenic cells and organisms generated from such cells. These methods include physical, non-biological systems such as electroporation, microinjection, calcium phosphate or polyethylene glycol (PEG) mediated DNA uptake or cell fusion, and microprojectile bombardment, and modified biological systems such as Agrobacterium-mediated T-DNA transfer to plant cells (for a general overview, see chapters 2 and 3 of "Plant Genetic Transformation and Gene Expression, A Laboratory Manual", ed. by Draper, J. et al., pub. by Blackwell Scientific Publications (1988); see also Potrykus, et al., "Direct Gene Transfer: State of the Art and Future Potential", *Plant Mol. Biol. Rep.* 3: 117–128 (1985)).

The methods which have been developed have allowed the stable transformation of a wide variety of cells and organisms with exogenous DNA. In particular, the development of physical techniques such as "biolistics" has overcome apparent host-range limitations imposed by biological systems. However, a common deficiency of these physical methods is that they do not provide any means for ordered integration of the delivered nucleic acid into the cell genome. Consequently these methods must depend upon uncontrolled integration of the delivered nucleic acid by poorly understood mechanisms, causing exogenous DNA to be integrated as multiple copies of random fragments usually at a single site in the cell genome.

Improving the predictability of stable transformation events arising from the physical introduction of exogenous nucleic acid into the cell would significantly improve the utility and overall efficiency of these processes for producing genetically stable transformed cells or organisms exhibiting stable expression of transgenes. One approach which has been taken to accomplish this goal has been to combine proteins which promote transformation and/or integration in biological systems with non-biological delivery techniques. In order to achieve the desired effect, it has been considered necessary to associate the proteins themselves with the exogenous DNA molecules prior to delivery to the transformation target cell, thus mimicking as closely as possible the biological system from which the proteins are derived (see, e.g. international application no. PCT/EP94/02566 to Hohn et al. published Feb. 23, 1995 as WO 95/05471; international application no. PCT/US95/07543 to Conary, J. et al. published Dec. 21, 1995 as WO 95/34647).

The Agrobacterium plant transformation system mentioned above is widely used for the stable transformation of higher plants. In this system genes to be transferred are carried by the T-DNA, a well-defined region of the Agrobacterium Ti plasmid. The Ti plasmid also contains a virulence (vir) region, which encodes proteins involved in the transformation via Agrobacterium of plant cells. At least one of these proteins, VirD2 is involved in targeting to the plant nucleus and integration into the plant genome (Tinland et al. (1992) *Proc. Natl. Acad. Sci. USA* 89: 7442; Tinland et al. (1995) *EMBO J.* 14: 3588–3595). WO 95/05471, the contents of which is herewith incorporated by reference, discloses a method for producing stably transformed plant material, including phenotypically normal looking and preferably fertile plants, which method does not involve Agrobacterium transformation. In particular, it discloses a specifically adapted nucleic acid/protein complex comprising a chimeric recombinant nucleic acid, which may comprise, for example, an expressible DNA or an oligonucleotide operably linked to suitable plant expression signals involving promoter and termination sequences and covalently associated therewith a VirD2, and, optionally, VirE2 protein units. However, the teaching does not mention potential applicability of this transformation technique to the field of animal cells. Furthermore, it does not concern using specifically designed oligonucleotides as nucleic acid component of said complex in an antisense- , antigene- or oligozyme-approach for (transient) transfection/transformation of eukaryotic cells.

Since there exists a continuous need for further techniques which are useful for the introduction of nucleic acids into animal and plant cells, e.g. oligonucleotides for antisense- or antigene-approaches, or for the permanent transformation of animal cells, the object of the present invention is therefore to provide a new method for introducing nucleic acids into eukaryotic cells.

SUMMARY OF THE INVENTION

The present invention provides an improved method for delivering nucleic acids as nucleic acid/protein complex to eukaryotic cells, e.g. oligonucleotides or exogenous DNA for stably transforming or transiently transfecting/transforming animal, preferably mammalian cells. This improved method for example generally comprises providing to the cell targeted for transfection/transformation a specifically designed nucleic acid/protein complex comprising nucleic acids such as e.g. exogenous DNA or oligonucleotide desired to be introduced and, if desired, to be integrated in the later transformant.

For example, the present invention particularly provides an improved method for transiently transfecting/transforming or for stably transforming animal cells with exogenous nucleic acids such as e.g. DNA, which combines positive attributes of *Agrobacterium tumefaciens* mediated T-DNA transfer such as high-efficient nuclear targeting and integration, with non-biological delivery methods. This aspect of the invention e.g. comprises providing an animal cell with the exogenous DNA fragment desired to be introduced into the nucleus and integrated into the animal cell genome, bounded by T-DNA borders or functional parts thereof, along with at least one Agrobacterium-derived protein that targets said fragment to the nucleus and promotes the integration of the exogenous DNA into the host cell genome. The Agrobacterium-derived protein used according to the invention is selected from the group consisting of VirD1, VirD2, VirE2, and VirC. Preferably, a combination of VirD2 and either VirD1, VirC, VirE2, or a subcombination thereof, is used. Most preferably, use is made of the Agrobacterium-derived proteins VirD2 and VirE2 in combination, although in certain cases sole use of VirD2 may be sufficient.

According to the invention, the nucleic acid/protein complex comprising the exogenous nucleic acid, such as e.g. a DNA fragment bounded by T-DNA border sequences or functional parts thereof, may be delivered to the animal cell by non-biological means such as, but not restricted to, electroporation, microinjection, induced uptake, microprojectile bombardment, or other means as are known in the art.

In another aspect of the invention, animal cells or tissues stably transformed with a discrete DNA fragment are regenerated to produce transgenic animal organs or whole animals that stably express a desired homologous or heterologous nucleic acid and, in the latter case, pass it on to progeny in which stable expression of the transgene is inherited as a Mendelian trait.

Furthermore, the present invention provides novel means for the in vivo and ex vivo/in vitro transformation and integration or transient transfection/transformation of exogenous nucleic acids desired to be expressed within animal hosts or host cells, particularly for the purpose of gene therapy.

In another aspect, the present invention supplies the procedures for introducing small nucleic acid fragments into animal cells and plant material, for use in antisense, antigene, oligozyme or mutagenesis technology.

DETAILED DESCRIPTION OF THE INVENTION

The present invention provides an improved method for introducing nucleic acids as nucleic acid/protein complex to eukaryotic cells, e.g. oligonucleotides or exogenous DNA for stably transforming animal cells. "Nucleic acid(s)" as a component of "nucleic acid/protein complex" according to the present invention may be any type of single- or double-stranded nucleic acid, for example RNA, modified RNA or DNA, wherein DNA is the preferred form. This improved method for example generally comprises providing to the animal cell targeted for transformation a specifically designed nucleic acid/protein complex comprising exogenous nucleic acid desired to be integrated and expressed in the later transformant. In this context, the terms "expressed" or "expressible" used throughout the specification shall mean that a given nucleic acid can at least serve as target for transcription within the nucleus of a cell to be transiently or permanently transfected or transformed. The term "T-DNA border(s) or functional part(s) thereof" shall encompass the whole T-DNA border sequence(s) as well as those parts thereof which have functional consensus or cleavage site or binding domain sequence(s) necessary for a desired protein to interact with the nucleic acid according to the invention.

For example, the present invention particularly provides an improved method for transiently transfecting/transforming or for stably transforming animal cells with exogenous nucleic acids such as e.g. DNA, which combines positive attributes of *Agrobacterium tumefaciens* mediated T-DNA transfer and integration with non-biological delivery methods. This aspect of the invention comprises providing an animal cell with the exogenous DNA fragment desired to be integrated into the animal cell genome, bounded by T-DNA borders or functional parts thereof, along with at least one Agrobacterium-derived protein that promotes the integration of the exogenous DNA into the host cell genome.

The Agrobacterium-derived protein used according to the invention particularly includes VirD1, VirD2, VirE2, and VirC. Preferably, a combination of VirD2 and either VirD1, VirC, VirE2, or a subcombination thereof, is used. Most preferably, use is made of the Agrobacterium-derived proteins VirD2 and VirE2 in combination. However, in certain cases sole use of VirD2 may be sufficient and is also within the scope of the invention.

According to the present invention it has surprisingly been found that animal cells derived from various cell lines are susceptible for transformation by using the DNA/protein complex as disclosed in WO 95/05471 mentioned above, and can efficiently be transiently transfected by using a similar complex in which the nucleic acid component is in the form of an oligonucleotide enabling antisense-, antigene- and oligozyme-approaches. Furthermore, it has been found that the Agrobacterium derived virulence proteins, VirD1 and VirD2, interact when expressed in mammalian cells. In particular, the above main object underlying the present invention has thus been achieved by using the properties of proteins produced by the vir region of Agrobacterium such as, for example, VirD1, VirD2 and VirE2, but especially that of the VirD2 proteins, in non-Agrobacterium transformation of animal cells.

The nucleic acid/protein complex already disclosed in WO 95/05471 may be obained by first providing a recombinant nucleic acid construct that comprises in operable linkage to the elements already mentioned above at least one T-DNA border sequence or functional part thereof as a substrate in the VirD2 cleavage reaction. If the said substrate involves not the whole but only part of the T-DNA border sequence, it is to be ensured that the said partial sequence still comprises those parts of the T-DNA border sequence that encompass the recognition and cleavage site of the VirD2 protein.

The chimeric recombinant nucleic acid construct as described above is preferably a single stranded DNA construct. Also comprised within the scope of the invention is a double-standed molecule with a single-stranded overhang which is a substrate for VirD2, or a chimeric recombinant DNA construct negatively supercoiled (form I) containing border sequences or at least functional parts thereof as the preferred substrate for VirD1VirD2 catalyzed cleavage. According to a preferred embodiment of the invention said chimeric recombinant nucleic acid/protein complex further comprises VirE2 and/or any other nucleic acid binding protein, such as recA, which contributes to efficient nuclear import and which, preferably, is also able to protect the nucleic acid to be transformed or transfected from nuclease attack. Preferably, the invention thus provides use of a chimeric recombinant nucleic acid construct covalently associated with VirD2, and optionally VirE2, proteins for the transformation or transfection of animal cells ex vivo, in vitro and in vivo. In this context it is to be understood that the proteins mentioned hereinbefore as component of the nucleic acid/protein complex according to the invention shall also mean oligopeptides or derivatives derived therefrom or functional fragments thereof retaining at least one functional characteristic necessary to achieve the aims of the present invention.

For details concerning the preparation of nucleic acid/protein complexes which can be used according to the present invention reference is made to the complete disclosure of WO 95/05471. However, it has to be noted that the nucleic acid/protein complex according to the present invention preferably comprises both VirE2 and VirD2 proteins in order to achieve optimum delivery and/or transformation efficiency, although the sole use of the VirD2 protein in the complex, in particular if said complex comprises single-stranded oligonucleotides, is also within the scope of the present invention. With respect to the preparation of a complex in which the nucleic acid component is in the form of an oligonucleotide enabling antisense-, antigene- or oligozyme-approaches, it is clear for a person skilled in the art how to construct such a complex.

Upon using the DNA/protein complex according to WO 95/05471 for the transformation of animal cells, the transformation frequency and also the quality of the integrated DNA can be improved considerably. This is especially true with regard to stable transformation events, which occur more frequently as compared to conventional, non-protein associated DNA constructs.

The present invention thus comprises a method for introducing nucleic acids into cells, e.g. for transforming or transiently transfecting/transforming animal cells, comprising (a) preparing a chimeric recombinant nucleic acid construct that comprises in operable linkage to an expressible DNA or to an oligonucleotide at least one T-DNA border sequence or functional part thereof, which serves as a substrate in the VirD2 cleavage reaction, as defined hereinbefore;

(b) cleaving of the nucleic acid substrate prepared according to step (a) by means of VirD2 protein, which may be accompanied by further Vir proteins such as, for example VirD1 and/or VirE2 and/or any other nucleic acid binding protein, which is able to protect said nucleic acid from nuclease attack;

(c) introducing the thus cleaved nucleic acid comprising at least the VirD2 protein covalently bound to the 5' end of the cleavage site into the cells to be transformed or transfected by methods known in the art.

According to a preferred embodiment of the above method, cleaving of the nucleic acid substrate (b) is carried out in vitro.

According to the invention the nucleic acid/VirD2 protein complex is preferably accompanied by further Vir proteins, such as, for example, VirE2, which is known to bind to ssDNA, and/or VirD1. VirE2 can be purified by methods known in the art such as those described in Christie et al [J Bacteriol 170(6): 2659–2667 (1988)]. The purification of the VirD1 protein can be achieved according to the method disclosed in WO 95/05471, whereas VirD2 can be obtained as set forth in Pansegrau et al. [PNAS 90, 11538 (1993)].

As mentioned before, the main object of the present invention is the use of a nucleic acid/protein complex comprising operably linked to e.g. an expressible DNA or to an oligonucleotide at least one T-DNA border sequence or functional part thereof, and covalently associated therewith a VirD2 protein in a process for introducing nucleic acids into animal cells. The nucleic acid/VirD2 protein complex preferably contains non-covalently associated further Vir proteins such as, for example, VirD1 and/or VirE2, with VirE2 being most preferred, particularly if used in connection with single-stranded oligonucleotides.

The term "exogenous" DNA or nucleic acid used herein is meant to include any DNA or other nucleic acid that has been obtained by recombinant nucleic acid technology. The exogenous nucleic acid to be used in the process according to the invention for transforming or transfecting target cells may be either of homologous or heterologous origin with respect to the cell type involved or it may be of synthetic origin or both. The coding nucleic acid sequence can be constructed according to conventional methods, e.g. from genomic DNA, or from cDNA. Another possibility is the construction of a hybrid DNA sequence consisting of both cDNA and genomic DNA and/or synthetic DNA. The cDNA may originate from the same gene as the genomic DNA, or alternatively both the cDNA and the genomic DNA may originate from different genes. In any case, however, both the genomic DNA and/or the cDNA may each be prepared individually from the same or from different genes.

The term "synthetic" DNA or nucleic acid includes (a) nucleic acid sequences that have been prepared entirely or at least partially by chemical means and (b) antisense or sense oligonucleotides. For example, synthetic DNA sequences may be suitably used, e.g., for modifying native DNA sequences in terms of codon usage, expression efficiency, etc.

Another approach according to the present invention is to generate antisense or antigene RNA or ribozymes/oligozymes within a given host cell by introducing into said cell a nucleic acid with reverse orientation which may become part of the host cells genome. In this context, introducing nucleic acid fragments encoding antisense or antigene oligonucleotides or oligozymes corresponding to even less than 100 bp of a specific RNA or DNA to be targeted is sufficient for inhibiting or modulating translation.

If the nucleic acid sequence to be transferred into the recipient cell contains portions of more than one gene, these genes may originate from one and the same organism, from several organisms that belong to more than one strain, one variety or one species of the same genus, or from organisms that belong to more than one genus of the same or of another taxonomic unit (kingdom). Chimeric recombinant nucleic acid molecules that comprise an expressible DNA, but especially a structural gene, preferably a heterologous structural gene operably linked with expression signals active in recipient cells, such as enhancer, promoter and transcription termination sequences, as well as, optionally, with further coding and/or non-coding sequences of the 5' and/or 3' region such as e.g. signal sequence, may also be preferably used within the transformation process as part of the nucleic acid/protein complex used according to the present invention. It is often advantageous to incorporate a leader sequence between the promoter sequence and the adjacent coding DNA sequence, the length of the leader sequence being so selected that the distance between the promoter and the DNA sequence to be expressed is the optimum distance for expression of the associated structural gene.

Furthermore, the exogenous DNA or other nucleic acid forming part of the nucleic acid/protein complex may additionally comprise sequences encoding one or more selectable markers useful in screening for positive transformants. In general, these markers are proteins necessary for the survival or growth of transformed host cells grown in a selective culture medium. Host cells not transformed with the vector containing the selection gene will not survive in the culture medium. Typical selection markers encode proteins that confer resistance to antibiotics and other-toxins, e.g. ampicillin, hygromycin, neomycin, puromycin, methotrexate or tetracycline, complement auxotrophic deficiencies, or supply critical nutrients not available from complex media. Further examples of genes that confer antibiotic resistance include those coding for the kanamycin resistance (NPT II) gene derived from Tn5 (Bevan et al, Nature 304: 184–187 (1983)), and chloramphenicol acetyltransferase.

Suitable selectable markers for animal, particularly mammalian cells are those that enable the identification of cells competent to take up the nucleic acid encoding said selectable marker, such as dihydrofolate reductase (DHFR, methotrexate resistance), thymidine kinase, or genes conferring resistance to G418 or hygromycin (see e.g. Blochlinger and Diggelmann (1984), *Molecular and Cellular Biology* 4: 2929–2931; Robertson and Whalley (1988), *Nucl. Acids Res.* 16: 11303–11317; O'Brian et al. (1997), Gene 184: 115–120). The animal cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes a structural gene of interest desired to be expressed in the transformed cells. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA. For the purpose of screening transient expression of the desired gene introduced into a suitable animal host cell according to the invention the exogenous DNA may also comprise sequences encoding β-galactosidase, green fluorescent protein (gfp), or luciferase. Methods for the detection of the expression of said markers are well known in the art. Screening of animal cells and animals derived from such cells for the presence of specific nucleic acid sequences may also be performed by Southern analysis [Southern, J. Mol. Biol. 98: 503 (1975)]. Details of this procedure are given in Maniatis et al, Molecular Cloning: A Laboratory Manual, Cold Spring Harbor Laboratory, Cold Spring Harbor, N.Y. (1 989). This screening may also be performed by the use of Polymerase Chain Reaction procedures (PCR). PCR procedures are described in detail in Mullis et al, Meth. Enzymol. 155: 335–350 (1987)and Erlich, (ed.), PCR Technology, Stockton Press, New York (1989).

The expression signals active in target cells usually comprise a promoter that is recognised by the host organism and is operably linked to the DNA to be expressed in the transformant. Such a promoter may be inducible or constitutive. The promoters are operably linked to said DNA by removing the promoter from the source DNA by restriction enzyme digestion and combining the isolated promoter sequence with the expressible DNA sequence. Both the native promoter sequence of the structural gene of interest and many heterologous promoters may be used to direct amplification and/or expression of said structural gene. Suitable promoters for animal and in particular mammalian hosts are those derived from the genomes of viruses such as polyoma virus, adenovirus, fowlpox virus, bovine papilloma virus, avian sarcoma virus, Rouse sarcoma virus (RSV), cytomegalovirus (CMV), a retrovirus and Simian Virus 40 (SV40), from heterologous mammalian promoters such as the β-actin promoter or a very strong promoter, e.g. a ribosomal protein promoter, and from the promoter normally associated with structural gene sequence to be expressed, provided such promoters are compatible with the host cell systems.

The transcription of an exogenous DNA encoding the desired structural gene can be increased by inserting an enhancer sequence into the DNA as a component of the nucleic acid/protein complex according to the invention. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the recombinant chimeric sequence at a position 5' or 3' to the coding DNA sequence, but is preferably located at a site 5' from the promoter.

Host cells to which nucleic acids can be delivered by a method according to the invention include insect and vertebrate cells. In recent years propagation of vertebrate cells in culture (tissue culture) has become a routine procedure. Examples of useful vertebrate host cell lines are epithelial or fibroblastic cell lines such as Chinese hamster ovary (CHO) cells, COS1 cells (monkey kidney cells transformed with SV40 T-antigen), CV1 cells (parent line of the former), Rat1 (rat fibroblast) cells, NIH 3T3 cells, HeLa cells, LLC-Pk1 (pig kidney epithelial) cells or 293T cells. The host cells referred to in this disclosure comprise cells in in vitro/ex vivo culture as well as cells that are within a host animal.

According to a further aspect of the present invention relating to antisense-, antigene- or oligozyme-approaches, the group of host cells which can be targeted also includes plant cells or tissues, which preferably can be regenerated to whole plants.

Especially suitable for use in the process according to the invention are all those structural genes which upon expression produce proteins or polypeptides which are beneficial for the transformed cells, tissues or animals, e.g. which compensate eventual mutatations, or which have pharmacological properties and could be used as pharmaceutical agents in the treatment of diseases. Examples for such structural genes include those encoding hormones, immunomodulators and other physiologically active substances.

The genes that particularly come into consideration within the scope of this invention therefore include, but are not limited to, for example, mammal-specific genes, such as the insulin gene, the somatostatin gene, the interleukin genes, the t-PA gene, etc., or genes of microbial origin, such as the NPT II gene, etc. and synthetic genes, such as the insulin gene, etc.

Apart from naturally occurring structural genes that code for a useful and desirable property or a pharmacological agent, within the scope of this invention it is also possible to use genes that have been modified previously in a specific manner using chemical or genetic engineering methods.

Furthermore, the broad concept of the present invention also includes genes that are produced entirely or partially by chemical synthesis. Genes or DNA sequences that may be used within the scope of the present invention are therefore both homologous and heterologous gene(s) or DNA and also synthetic gene(s) or DNA according to the definition given within the scope of the present invention. The insulin gene may be mentioned at this point as an example of a synthetic gene.

Alternatively, oligonucleotides can be used corresponding in sequence to a cellular sequence to be targeted, either in the same (antigene) coding direction, as such or carrying a mutation, or in the antisense coding direction.

Possible methods for the direct transfer of the nucleic acid/protein complex according to the invention into a cell comprise, for example, the treatment of cells using procedures that modify the plasma membrane, for example, polyethylene glycol treatment, liposome-based technologies, heat shock treatment or electroporation, or a combination of those procedures (see e.g. Chu et al. (1987), Nucl. Acids Res. 15: 1311–1326; Hodgson and Solaiman (1996), Nature Biotech. 14: 339–342; Shillito et al. (1985), Bio Technology 3: 1099–1103).

In the electroporation technique, cells together with the nucleic acid/protein complex used according to the invention are subjected to electrical pulses of high field strength. This results in a reversible increase in the permeability of biomembranes and thus allows the insertion of the nucleic acid/protein complex according to the invention. Electroporated cells renew their cell membrane, divide and form aggregates or monolayers of transformed cells. Selection of the transformed cells can take place with the aid of the above-described phenotypic markers.

A further method for the direct introduction of the nucleic acid/protein complex used according to the invention into cells, which is based on purely chemical procedures and which enables the transformation to be carried out very efficiently and rapidly, is described in Jordan et al. (1996), Nucl. Acids Res. 24: 596–601).

Also suitable for the transformation of e.g. animal cells is direct gene transfer using co-transformation [Schocher RJ et al, Bio/Technology, 4:1093–1096 (1986)]. Co-transformation is a method that is based on the simultaneous taking up and integration of various DNA molecules (non-selectable and selectable genes) into the recipient's genome and that therefore allows the detection of cells that have been transformed with non-selectable genes.

Further means for inserting the nucleic acid/protein complex used according to the invention directly into a cell comprise using purely physical procedures, for example by microinjection using finely drawn micropipettes [Neuhaus et al (1987)] or by bombarding the cells with microprojectiles that are coated with the transforming or transiently transfecting nucleic acid ["Microprojectile Bombardment"; Wang Y-C et al, Plant Mol. Biol. 11: 433–439 (1988)] or are accelerated through a nucleic acid containing solution in the direction of the cells to be transformed by a pressure impact thereby being finely atomized into a fog with the solution as a result of the pressure impact [EP-A-434,616]. Microprojectile bombardment has been advanced as an effective transformation technique for e.g. animal cells.

The list of possible transformation and transfection methods given above by way of example is not claimed to be complete and is not intended to limit the subject of the invention in any way.

The present invention also concerns the preparation of transgenic animal cells, including oocytes, spermatocytes and zygotes etc., transgenic organs and transgenic animals, as well as the cells and animals obtained by use of a method according to the invention.

A transgenic animal which can be produced according to the invention preferably is a mammal, with pigs, rodents and ruminants being most preferred. Additionally, the present invention can be used for somatic gene therapy in humans, which use is also part of the invention.

The method according to the invention can be advantageously used to increase The transformation efficiency of non-Agrobacterium mediated transformation processes, in that, for example, less transforming DNA is needed as compared to the conventional techniques. In addition the quality of the integrated DNA can be improved by the precision of the integration process, and possible rearrangements which are likely to happen to naked DNA can be avoided.

The method according to the invention thus provides valuable means for the treatment of various disorders susceptible to gene therapy and enables the production of transgenic animals, where the efficiency of integration of naked DNA is a limiting factor. Furthermore, the method is useful in the treatment of cancer cells, as a new non-viral system without LTR and possible hazards connected with them. A special feature of the complexes used according to the invention is their DNAse resistance and their ability to also target non dividing cells, due to their nuclear targeting potential.

The invention is further described, for the purposes of illustration only, in the following examples.

EXAMPLES

Example 1

Construction of Plasmids for Monitoring the Intracellular Localisation of VirD2 Protein The N terminal gfp fusion vector pβact-NGFP, containing the β-actin promoter and SV40 terminator is used (Ludin et al. (1996) Gene 173: 107–111). virD2 is cloned as entire gene, or as a mutant gene containing only the N-terminal (Rossi et al. (1993) Mol. Gen Genet. 239: 345–353), or C terminal NLS, or mutant gene in which both nuclear localisation (NLS) sequences are deleted. For detection of the protein by anti-VirD2 antibodies, virD2 is cloned in mammalian expression vector pcDNA3 (Invitrogen).

Example 2

Construction of Plasmid for Monitoring the Intracellular Localisation of VirD1 Protein VirD1 gene is amplified by PCR using pVCK225 (V. C. Knauf and E. W. Nester, Plasmid 8, 45–54 (1982)) as a template. The heamagglutinin (HA) epitope tagged construct pHA-D1 is prepared by ligating an HA epitope encoding oligonucleotide to the 5' end of the virD1 PCR product, in-frame with the initiator methionin codon, in the mammalian expression vector pcDNA3 (Invitrogen).

Example 3

Monitoring Intracellular Localization of VirD2 Protein in Mammalian Cells

When overexpressed in mammalian cells (HeLa, 293), VirD2 protein shows exclusively nuclear localisation, which is monitored either by GFP-VirD2 fusion, or by immunoreaction of virD2 transfected cells with anti-VirD2 antibodies. The presence of any of two localisation signals, on the N- and C- terminus of the VirD2, is sufficient for efficient nuclear localisation, while deletion of both NLS sequences renders the protein cytoplasmic. Overexpression of VirD2 protein in mammalian cells does not have a visible negative effect on their growth and division.

Example 4

Monitoring Intracellular Localisation of VirD1 Protein in Mammalian Cells

When overexpressed in mammalian cells (HeLa, 293), VirD1 protein shows exclusively cytoplasmic localisation which is monitored by immunoreaction of pHA-D1 transfected cells with an anti-HA epitope 12CA5 monoclonal antibody (Boehringer). Overexpression of VirD1 protein in mammalian cells does not have a visible negative effect on their growth and division.

Example 5

Production of M13 ssDNA for Analysis of Nuclear Targeting by Gene Expression

First, the gfp cycle3 gene is cloned from pαGFP cycle3 vector (Crameri et al. (1996) Nature Biotechnology 14:

315–319) into the SmaI site of pBluescript SKII as StuI fragment. StuI ends are blunted with T4 DNA polymerase. Then, gfpcycle3 gene is cloned as NotI/PstI fragment in the coresponding sites of M13 vector containing the right border sequence, named Y3 (M13RBMCS). Phage infection is done in E. coli NM522. Bacteria are grown for 5h at 37° C. and ssDNA isolated from the supernatant by Qiagen plasmid purification kit.

Example 6

Production of the Complexes Used in Direct Assay for Protein Import and Microinjection DNA is fluorescently labeled by introducing rhodamine dUTP into the PCR reaction product. The primers used for the PCR both contain the right border (RB) sequence at each extremity of DNA, in opposite orientation. The PCR product is then heat denatured and the resulting ssDNA of 1 kb length reacted with VirD2 protein for 1 h at 37° C. The reaction is stopped on ice and and incubated on ice with VirE2 protein, for another 30'.

Example 7

Microinjection of the T-DNA Complexes into Mammalian Cells

T-DNA complexes, produced in the same way as explained above, are microinjected into the cytoplasm of mammalian cells (HeLa) and nuclear targeting is monitored. Since low amounts of ssDNA are used in this assay, intensity of the signal has to be increased by anti-rhodamine antibodies. Nuclear targeting is also being monitored by using an active gene present on ssDNA. The green-fluorescent protein gene (gfp) is cloned in a M13 vector containing the right border sequence. (Function of the gfp is tested by microinjection of both ds, and ssDNA into the nucleus of HeLa cells.) Phage ssDNA is processed with VirD2, and VirE2 is added. Complexes are microinjected in the cytoplasm of HeLa cells and expression of GFP is monitored after 12–24h.

Example 8

Stable Integration of T-DNA Derived from the Artificial Complexes

For testing the ability of artificial complexes to integrate T-DNA in the mammalian genome, a hygromycin reporter gene is cloned in an M13 vector containing the right border sequence. Alternatively, DNA is produced by PCR, in which each of the primers contain the right border sequence. ssDNA is complexed with VirD2 and VirE2 proteins, and injected in the cytoplasm of HeLa cells. After selection resistant clones are picked and their DNA analysed for the pattern of integration.

Example 9

Nuclear Targeting of the T-DNA Complexes

Artificial complexes, consisting of VirD2 protein covalently attached to the single stranded DNA, and VirE2 protein, are tested in direct assay of protein import into HeLa nuclei. ssDNA is rhodamine labelled by PCR and digitonin permeabilised HeLa nuclei are used as a target (Adam et al. (1990) *Journal of Cell Biology* 111: 807–816). Indeed, the T-DNA complex is efficiently targeted to the HeLa nuclei. Efficient targeting is dependent on the function of nuclear localisation signal of VirD2.

Example 10

Analysis of VirD2-VirD2 and VirD1 -VirD2 Interactions in Mammalian Cells

Protein-protein interactions are verified in mammalian system by studies of subcellular localisation of VirD1, VirD2 and its derivative deleted in both NLSs in HeLa and HEK293 cells using GFP-VirD2 fusion for localisation of VirD2 and HA epitope for localisation of VirD1. VirD2 protein localises exclusively in the nuclei when expressed in mammalian cells. Deletion of both NLS sequences renders the protein cytoplasmic. However, this double mutant is translocated to the nucleus in the presence of wild type VirD2 protein, indicating VirD2-VirD2 interaction in mammalian cells. Also the VirD1 protein, by itself localising in the cytoplasm, moves to the nucleus when co-expressed with the wild type VirD2 protein, indicating VirD1-VirD2 interaction in mammalian cells.

Example 11

Purification of the VirD2 Protein

A sequence tag encoding six histidine residues is added to the C-terminal of the VirD2 protein. The recombinant protein is expressed in *E.coli* BL21 and purified by histidine-nickel affinity chromatography followed by gel filtration and heparin affinity chromatography according to standard methods known in the art.

Example 12

Production of Single Stranded VirD2 Processing Substrates Containing the Hygromycin Resistance Gene First, the hygromycin resistance gene containing the DraI/FspI restriction fragment of pTK-Hyg (Clonetech) is cloned into the HincI site of the Y3 vector (defined in example 5). The recombinant plasmid is transformed into *E.coli* NM522 and ss phage DNA is isolated. Oligonucleotides complementary to the EcoRV and KasI sites in the phage DNA are used to mediate the cleavage of the ss DNA by EcoRV and KasI restriction nucleases. The obtained EcoRV/KasI ssDNA fragment contains the hygromycin resistance gene positioned downstream of the right border sequence.

Example 13

Transfecion of Artificial T-DNA Complexes into HeLa Cells

The ssDNA EcoRV/KasI fragment is reacted with either VirE2 or VirD2 proteins alone or is first reacted with virD2 followed by reaction with virE2. The resulting protein:ss-DNA complexes as well as unreacted ssDNA are transfected into HeLa cells using Fugene-6 transfection reagent (Boehringer-Mannheim). Hygromycin resistant clones are selected in two independent experiments. The number of hygromycin resistant clones obtained is significantly higher for cells transfected with ssDNA+VirD2 and ssDNA+VirD2+VirE2 complexes (table 1) suggesting that the proteins facilitate stable integration of the hygromycin resistance gene by either protecting the ssDNA from degradation by host cells nucleases and/or by facilitating the nuclear import of the complex. Transgene copy number and transgene integrity is analyzed for several lines from experiment 1. Preliminary data indicate that the hygromycin gene integrates at single distinct loci in all line analyzed so far. Preliminary results also indicate that both VirE2 and VirD2 proteins protect the ssDNA prior to its integration into the genome. As expected the protective action of VirE2 seems to result from the protein coating the entire length of the ssDNA, whereas the covalent attachment of the VirD2 protein to the 5' end of the T-DNA specifically protects the 5' end.

TABLE 1

Number of hygromycin resistant clones obtained in transfection experiments

| Transfected DNA (complex) | Resistant clones Experiment 1 | Resistant clones Experiment 2 |
|---|---|---|
| ssDNA | 6 | 11 |
| ssDNA + VirE2 | 6 | 29 |
| ssDNA + VirD2 | 7 | 34 |
| ssDNA + VirD2 + VirE2 | 12 | 44 |

What is claimed is:

1. A method for introducing nucleic acids into mammalian cells, comprising:

(a) preparing a chimeric recombinant nucleic acid construct that comprises in operable linkage to an expressible DNA or to an oligonucleotide at least one T-DNA border sequence or functional part thereof, which serves as a substrate in the VirD2 cleavage reaction;

(b) cleaving of the nucleic acid substrate prepared according to step (a) by means of VirD2 protein, wherein the cleavage of the substrate by means of VirD2 is carried out in the presence of wild-type VirE2; and (c) introducing the cleaved nucleic acid comprising the VirD2 protein covalently bound to the 5' end of the VirD2 cleavage site and wild-type VirE2 protein into the cells.

2. A method according to claim 1, wherein the transformation or transfection is achieved by a method selected from the group consisting of microinjection, electroporation of cells, direct gene transfer and ballistic particle acceleration.

3. The method of claim 1, wherein the expressible DNA sequence encodes for a structural gene.

4. The method of claim 1, wherein the cleavage of the substrate by means of VirD2 in the presence of wild-type VirE2 is carried out in the presence of at least one other nucleic acid binding protein.

5. The method of claim 4, wherein the at least one other protein is selected from the group of VirC and VirD1.

6. The method of claim 3, wherein the structural gene is a heterologous structural gene.

* * * * *